(12) United States Patent
Cristiani et al.

(10) Patent No.: US 11,925,799 B2
(45) Date of Patent: Mar. 12, 2024

(54) MUSCLE-STIMULATING ATHLETIC WEAR

(71) Applicants: Nicole Britta Cristiani, Marina del Rey, CA (US); Nino Cristiani, Marina del Rey, CA (US)

(72) Inventors: Nicole Britta Cristiani, Marina del Rey, CA (US); Nino Cristiani, Marina del Rey, CA (US)

(73) Assignees: Nicole Britta Cristiani, Beverly Hills, CA (US); Nino Cristiani

( * ) Notice: Subject to any disclaimer, the term of this patent is extended or adjusted under 35 U.S.C. 154(b) by 274 days.

(21) Appl. No.: 17/183,197

(22) Filed: Feb. 23, 2021

(65) Prior Publication Data
US 2021/0282473 A1 Sep. 16, 2021

Related U.S. Application Data

(60) Provisional application No. 62/989,475, filed on Mar. 13, 2020.

(51) Int. Cl.
*A61N 1/04* (2006.01)
(52) U.S. Cl.
CPC ......... *A61N 1/0452* (2013.01); *A61N 1/0484* (2013.01); *A61N 1/0492* (2013.01)
(58) Field of Classification Search
CPC .................... A61N 1/0452; A61N 1/0484
See application file for complete search history.

(56) References Cited

U.S. PATENT DOCUMENTS

| 4,381,012 | A | * | 4/1983 | Russek | A61N 1/0484 600/382 |
| 5,147,261 | A | * | 9/1992 | Smith | A61F 5/028 482/106 |
| 5,484,395 | A | * | 1/1996 | DeRoche | A61F 5/028 2/311 |
| 5,628,721 | A | * | 5/1997 | Arnold | A61F 5/028 128/118.1 |
| 5,766,236 | A | * | 6/1998 | Detty | A61N 1/321 607/152 |
| 6,728,577 | B2 | * | 4/2004 | Minogue | A61N 1/321 607/148 |
| 9,789,308 | B2 | * | 10/2017 | Southwell | A61N 1/0484 |
| 9,827,418 | B2 | * | 11/2017 | Southwell | A61N 1/0452 |
| 9,861,816 | B2 | * | 1/2018 | Southwell | A61N 1/36034 |
| 9,962,544 | B2 | * | 5/2018 | Southwell | A61N 1/0456 |

(Continued)

*Primary Examiner* — Eric D. Bertram
(74) *Attorney, Agent, or Firm* — Edison Law Group

(57) ABSTRACT

A muscle-stimulating waist trainer is an apparatus that strengthens and tones abdominal muscles. The apparatus includes a piece of athletic wear, a plurality of muscle-stimulation pads, a pair of conductive snaps, and a controller unit. The piece of athletic wear covers and compresses the body of a user. The piece of athletic wear positioned the plurality of muscle-stimulation pads against a desired muscle group. The piece of athletic wear may be, but is not limited to, a pair of athletic pants, a waistband, and an arm sleeve. The plurality of muscle-stimulation pads stimulates the desired muscle group, promoting increased tension for the desired muscle group and a toned physique after prolonged use. The pair of conductive snaps mounts the controller unit onto the piece of athletic wear and transmits the current from the controller unit through the athletic wear, and to the plurality of muscle-stimulation pads.

12 Claims, 12 Drawing Sheets

(56) References Cited

U.S. PATENT DOCUMENTS

| | | | |
|---|---|---|---|
| 10,279,174 B2* | 5/2019 | Southwell | A61N 1/0452 |
| 10,279,175 B2* | 5/2019 | Southwell | A61N 1/048 |
| 2005/0055054 A1* | 3/2005 | Yu | A61N 1/322 |
| | | | 607/2 |
| 2010/0049027 A1* | 2/2010 | Teschner | A61B 5/411 |
| | | | 600/390 |
| 2012/0116477 A1* | 5/2012 | Crowe | A61N 1/321 |
| | | | 607/46 |
| 2016/0235981 A1* | 8/2016 | Southwell | A61N 1/36007 |
| 2017/0182318 A1* | 6/2017 | Fisher | A61N 1/0484 |
| 2018/0133468 A1* | 5/2018 | Southwell | A61N 1/0452 |
| 2018/0154145 A1* | 6/2018 | Southwell | A61N 1/36034 |

* cited by examiner

MUSCLE-STIMULATING ATHLETIC WEAR

The current application claims a priority to the U.S. provisional patent application Ser. No. 62/989,475 filed on Mar. 13, 2020.

FIELD OF THE INVENTION

The present invention generally relates to exercise devices. More specifically, the present invention is a muscle-stimulating athletic wear.

BACKGROUND OF THE INVENTION

Toning and having a fit physique have always been a typical fitness goal for most individuals. Gym machines and classes are a standard tool for fitness maintenance and weight loss, as well as at-home regimens and at-home workout devices. A trouble spot for most individuals, because of faulty diets, is the abdominal region. No matter how much an individual works out, the abdominal region typically needs more effort and direct stimulation in order to see real results.

An objective of the present invention is to provide a system for a conductive layer arrangement that is integrated into a waist trainer. The present invention includes a sticker-like design that utilizes a proprietary mix of conductive ink, other materials, and protective tape to create a durable and waterproof conductive circuit. The present invention also includes a process to transfer the conductive circuit onto a fabric. The present invention is designed to deliver electrical signals to the abdominal area without having to utilize multiple attachments. The present invention preferably includes a signal generator which can be removably connected to the conductive layer arrangement integrated onto the garment.

DETAIL DESCRIPTIONS OF THE INVENTION

Figure 1:
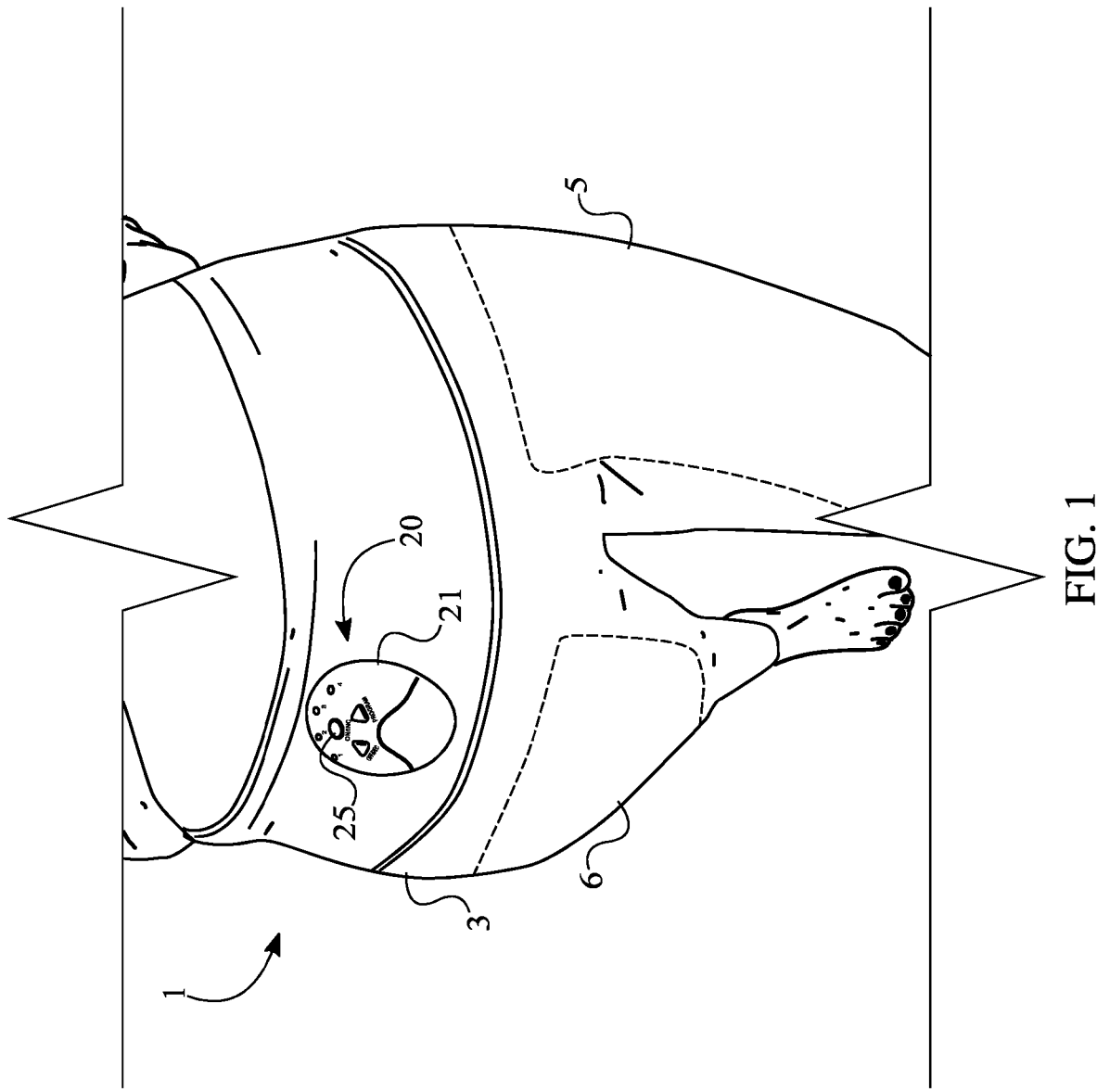
FIG. 1 is a front side view of a first embodiment of the present invention.

All illustrations in the drawings are for the purpose of describing selected versions of the present invention and are not intended to limit the scope of the present invention.

The present invention is muscle-stimulating athletic wear. The present invention directly targets a desired muscle region of a user while working out or while doing everyday tasks. Such a desired muscle region includes, but is not limited to, abdominal muscles, bicep and triceps muscles, and hamstring and glute muscles. The present invention is ideal for strengthening and toning muscles. The present invention promotes sweating around the desired muscle region as well as shapes the body of a user. Furthermore, the present invention stimulates the desired muscles of a user to increase tension for the corresponding muscles. This stimulation facilitates a toned physique. In order to safely stimulate a desired muscle region while promoting an hourglass shaped physique, the present invention comprises a piece of athletic wear 1, a plurality of muscle-stimulation pads 16, a pair of conductive snaps 19, and a controller unit 20, seen in FIG. 1, FIG. 2, FIG. 3, FIG. 5, FIG. 6, FIG. 9, FIG. 10, FIG. 11, and FIG. 12. The piece of athletic wear 1 shapes the desired area of the body of a user and promotes swearing around the corresponding area of the body. The piece of athletic wear 1 also positions the plurality of muscle-stimulation pads 16 against the desired area of the body. The piece of athletic wear 1 comprises an inner surface 2 and an outer surface 3. The inner surface 2 is oriented towards the body of the user, and the outer surface 3 is oriented away from the body of the user. The plurality of muscle-stimulation pads 16 transfers a safe electric charge to the desired muscles of the user. The plurality of muscle-stimulation pads are each preferably a piece of silver-embedded stretch fabric, which is electrically conductive. The pair of conductive snaps 19 mounts the controller unit 20 with the piece of athletic wear 1 and delivers the charge from the controller unit 20, through the piece of athletic wear 1, and to the plurality of muscle-stimulation pads 16. The controller unit 20 provides a power supply for the plurality of muscle-stimulation pads 16. Moreover, the controller unit 20 comprises a housing 21, a pair of snap leads 22, a microcontroller 23, and a power source 24, seen in FIG. 10 and FIG. 12. The housing 21 contains the microcontroller 23 and the power source 24. The pair of snap leads 22 mounts the housing 21 onto the piece of athletic wear 1 and serves as the electrical connection for the power source 24 with the pair of conductive snaps 19. The microcontroller 23 manages the connection between the power source 24 and the pair of conductive snaps 19. The power source 24 provides the necessary power to charge the plurality of muscle-stimulation pads 16. The power source 24 is preferably at least one portable battery. However, in alternate embodiments of the present invention, the power source 24 may be a rechargeable battery as well.

The overall configuration of the aforementioned components directly targets and stimulates a desired muscle area. The pair of electrode pads press against the skin of the user, specifically the abdominal area of the user, as the plurality of muscle-stimulation pads 16 is fixed onto the inner surface 2, seen in FIG. 7 and FIG. 8. In order to charge the plurality of muscle-stimulation pads 16 with the controller unit 20, the pair of conductive snaps 19 is integrated through the piece of athletic wear 1. The present invention stimulates, and therefore tones, the desired muscle region of the user. The plurality of muscle-stimulation pads 16 is electrically connected to the pair of conductive snaps 19. The controller unit 20 connects onto and electrically connects with the pair of conductive snaps 19 as the pair of snap leads 22 is externally mounted with the housing 21. The power source 24 and the microcontroller 23 are mounted within the housing 21 in order to provide a compact controller unit 20 that protects and contains the power source 24 and the microcontroller 23. The user may operate the plurality of muscle-stimulation pads 16 as the pair of snap leads 22 is electronically connected with the microcontroller 23. The pair of snap leads 22 is electrically connected with the power source 24, thereby providing sufficient power to charge the plurality of electrode pads. The controller unit 20 may be connected and disconnected according to the discretion of the user as each of the pair of snap connectors are releasably engaged by a corresponding lead from the pair of snap leads 22.

Figure 8:
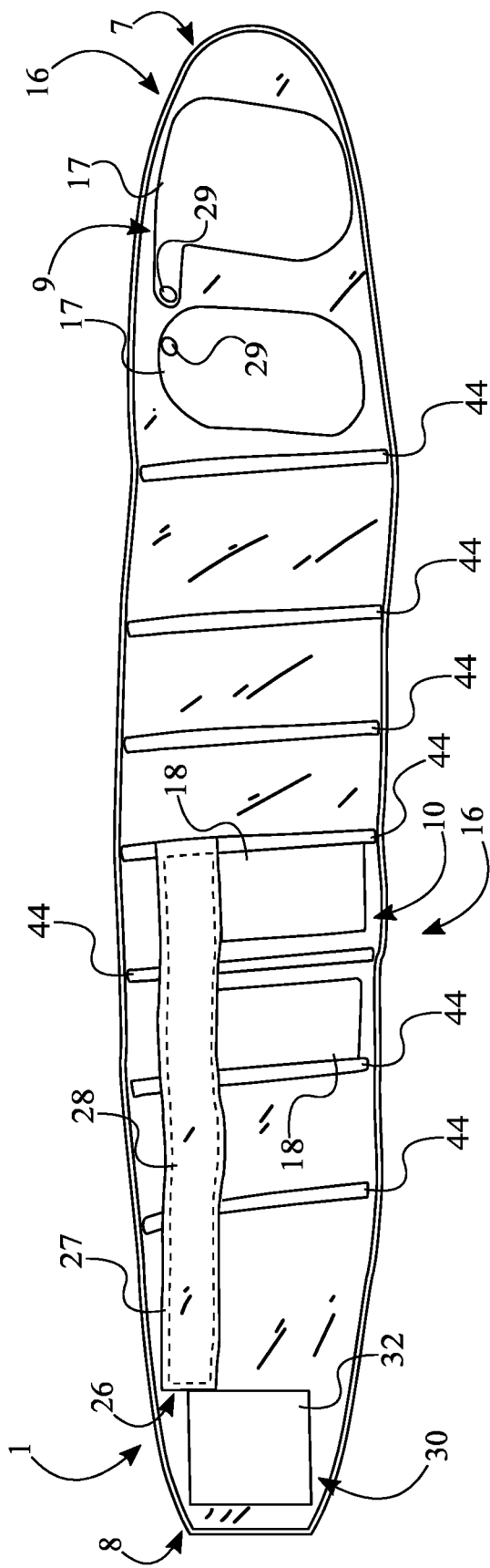
FIG. 8 is a rear side view of the second embodiment of the present invention with the first end of the waistband detached from the second end of the waistband.

The present invention further comprises at least one flat conductor 26, seen in FIG. 8. The plurality of muscle-stimulation pads 16 also comprises a plurality of first pads 17 and a plurality of second pads 18. The at least one flat conductor connects the plurality of second pads 18 with the pair of conductivity snaps. The plurality of first pads 17 and the plurality of second pads 18 each stimulate specific muscles of a desired region for full contact and even stimulation. Moreover, the at least one flat conductor 26 allows the plurality of second pads 18 to be positioned offset with the plurality of first pads 17 thereby effectively covering the desired muscle region. Both the plurality of first pads 17 and the plurality of second pads 18 are positioned adjacent to the pair of conductive snaps 19. The plurality of first pads 17 is preferably positioned adjacent with a conductive snap closest to the plurality of first pads 17. Likewise, the plurality of second pads 18 is preferably positioned adjacent with the remaining conductive snap. A continuous path for the electrical charge is maintained from the pair of conductivity snaps to the plurality of second pads 18 as the plurality of flat conductors is mounted onto the inner surface 2. More specifically, each of the plurality of first pads 17 are in direct electrical communication with the pair of conductivity snaps, and each of the plurality of second pads 18 is in indirect electrical communication with the pair of conductive snaps by the at least one flat conductor 26.

In the preferred embodiment of the present invention, the at least one flat conductor 26 comprises an insulative tape 27 and a strip of silver-embedded stretch fabric 28, also seen in FIG. 8. The insulative tape 27 protects the skin of the user from coming into contact with the strip of silver-embedded stretch fabric 28. The strip of silver-embedded stretch fabric 28 serves as a wire to connect a plurality of second pads 18 with the plurality of first pads 17 if the plurality of second pads 18 is positioned further along the piece of athletic wear 1. In order to deliver the charge from the pair of conductivity snaps to the plurality of second pads 18, the strip of silver-embedded stretch fabric 28 is electrically conductive. The strip of silver-embedded stretch fabric 28 is thermally adhered onto the inner surface 2 by the insulative tape 27, thereby isolating the strip of silver-embedded stretch fabric 28 with the insulative tape 27.

Figure 7:
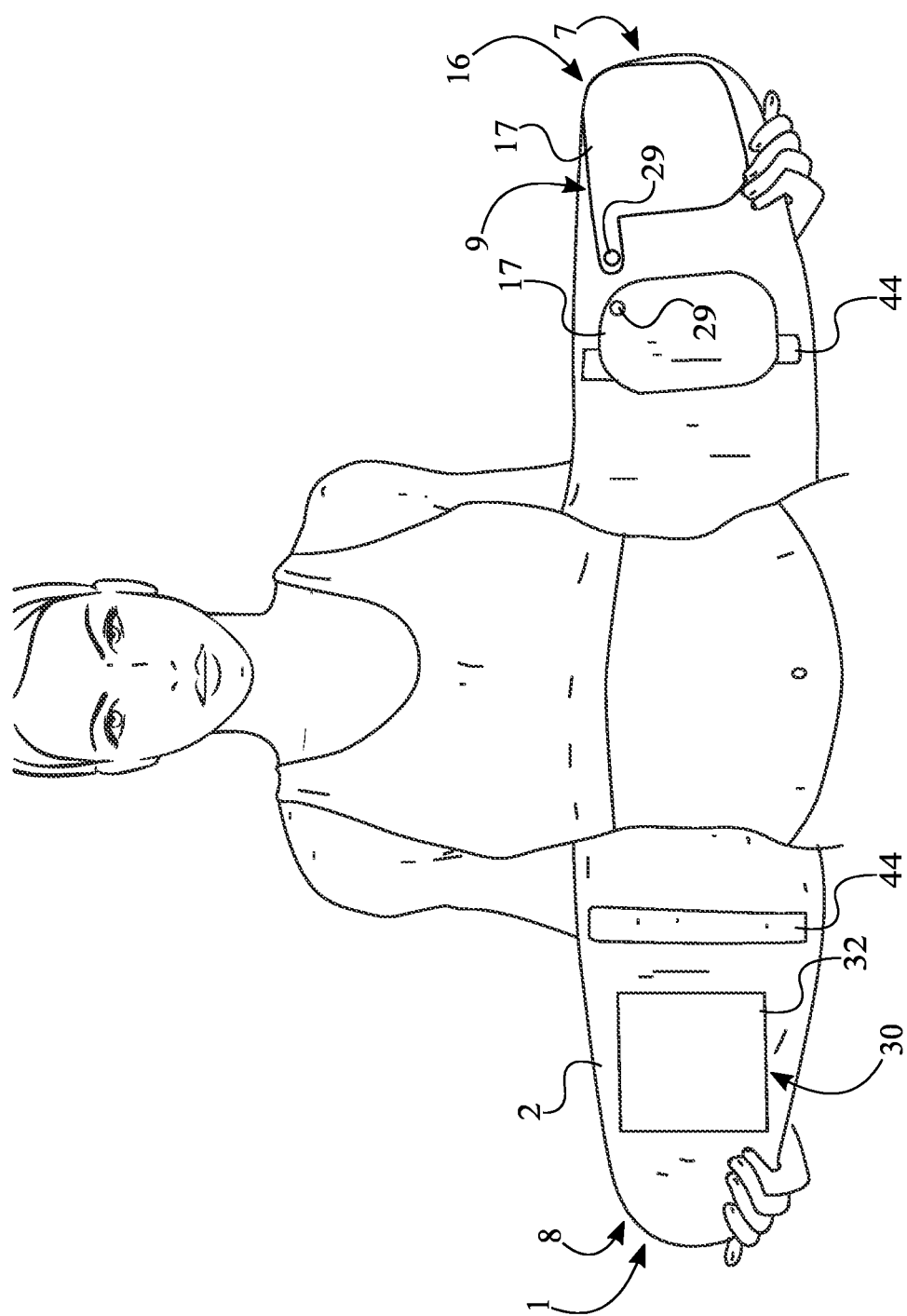
FIG. 7 is a front side view of the second embodiment of the present invention with the first end of the waistband detached from the second end of the waistband.
Figure 9:
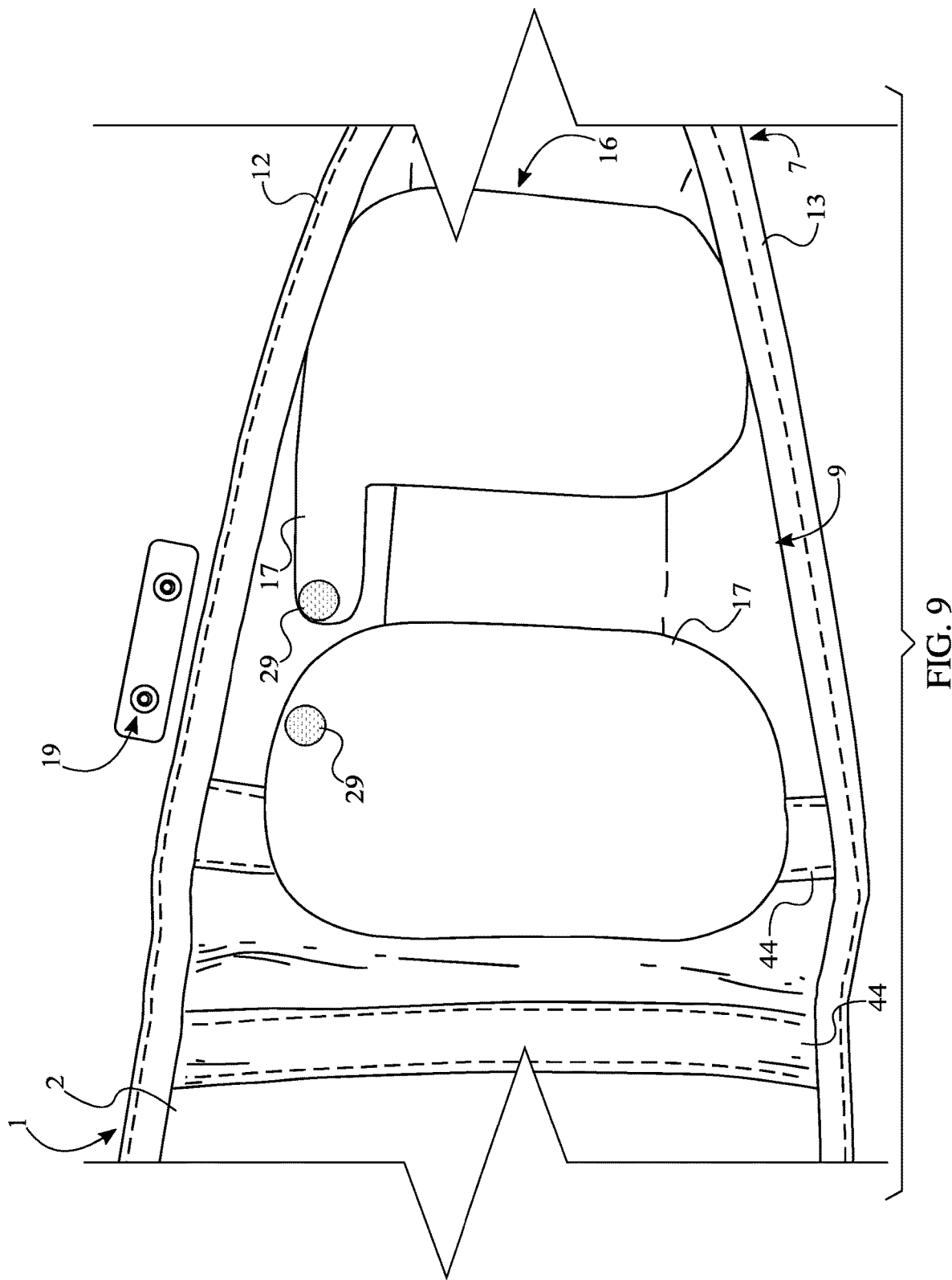
FIG. 9 is an enlarged exploded view for an inner surface of the waist band along the first end of the waistband of the present invention with a pair of conductive snaps mounted with an electrically-insulative support strip.
Figure 10:
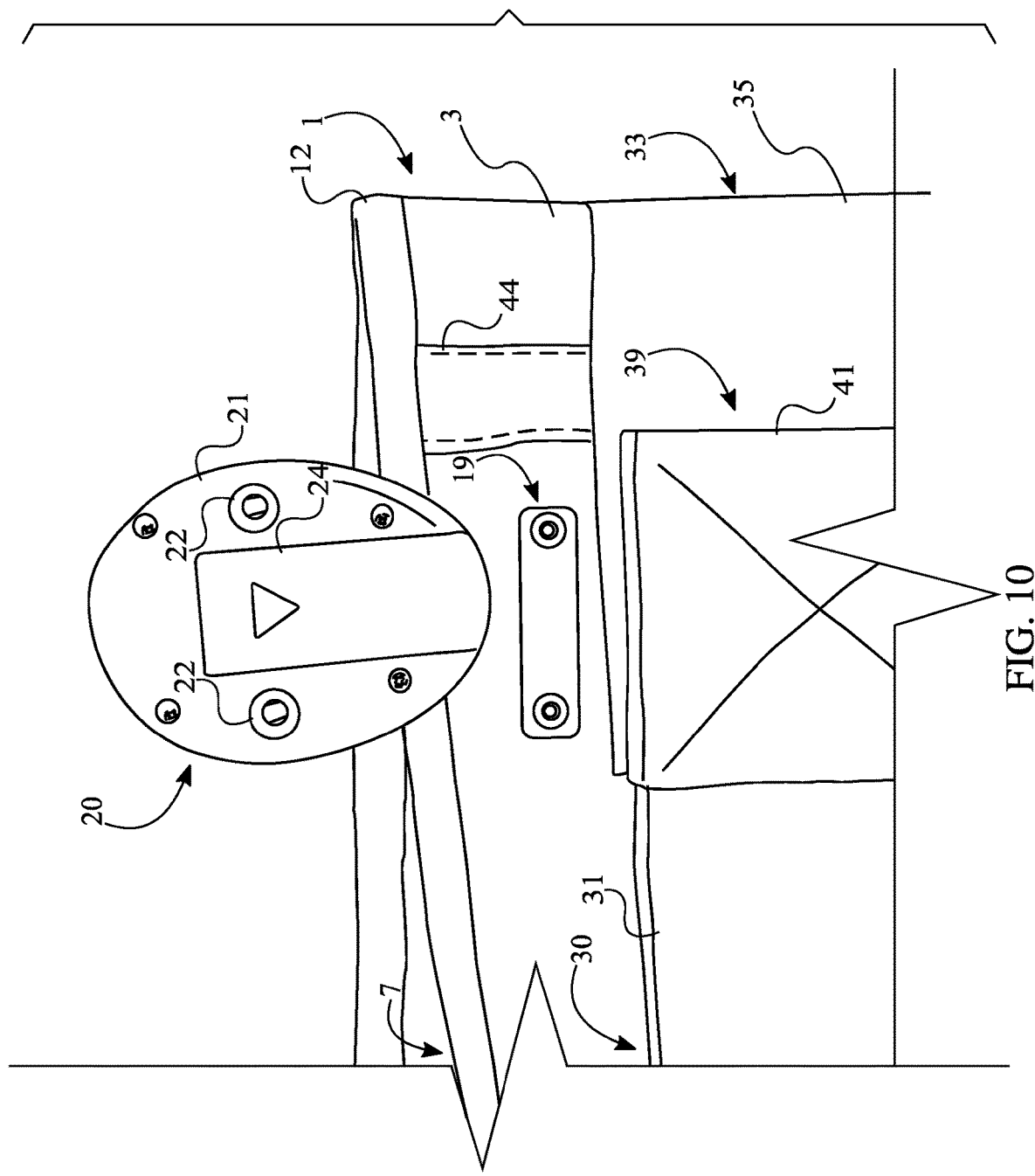
FIG. 10 is an enlarged view for an outer surface of the waist band along the first end of the waistband of the present invention with a controller unit detached with the pair of conductive snaps.

The safety of the present invention is further preserved while effectively electrically stimulating a desired muscle region of a user as the present invention further comprises a pair of electrically-insulative covers 29, seen in FIG. 7, FIG. 8, and FIG. 9. The pair of electrically insulative covers shields the pair of conductive snaps 19 from coming into direct contact with the skin of the user. In order to protect the skin of the user from coming into contact with the pair of conductive snaps 19, the pair of electrically-insulative covers 29 is positioned adjacent to the inner surface 2. More specifically, each of the pair of electrically-insulative covers 29 is mounted onto a corresponding snap from the pair of conductive snaps 19.

The user is able to control the functions of the controller unit 20, and consequently the plurality of muscle-stimulation pads 16 of the present invention, as the controller unit 20 further comprises at least one controller button 25, seen in FIG. 1, FIG. 3, FIG. 11, and FIG. 12. The at least one controller button 25 allows the user to turn off and turn on the plurality of muscle-stimulation pads 16, adjust the tempo of the electrical stimulation for the plurality of muscle-stimulation pads 16, adjust the intensity of the electrical stimulation of the plurality of muscle-stimulation pads 16 and so on. The pair of snap leads 22 is positioned offset from each other in order to charge the plurality of muscle-stimulation pads 16 simultaneously. In order for the user to easily access the at least one controller button 25 and operate the controller unit 20, the at least one controller button 25 is externally mounted with the housing 21 and is electronically connected with the microcontroller 23. More specifically, the at least one controller button 25 is electrically connected with the power source 24, thereby controlling the charge from the power source 24 to the plurality of muscle-stimulation pads 16 with the at least one controller button 25.

Figure 2:
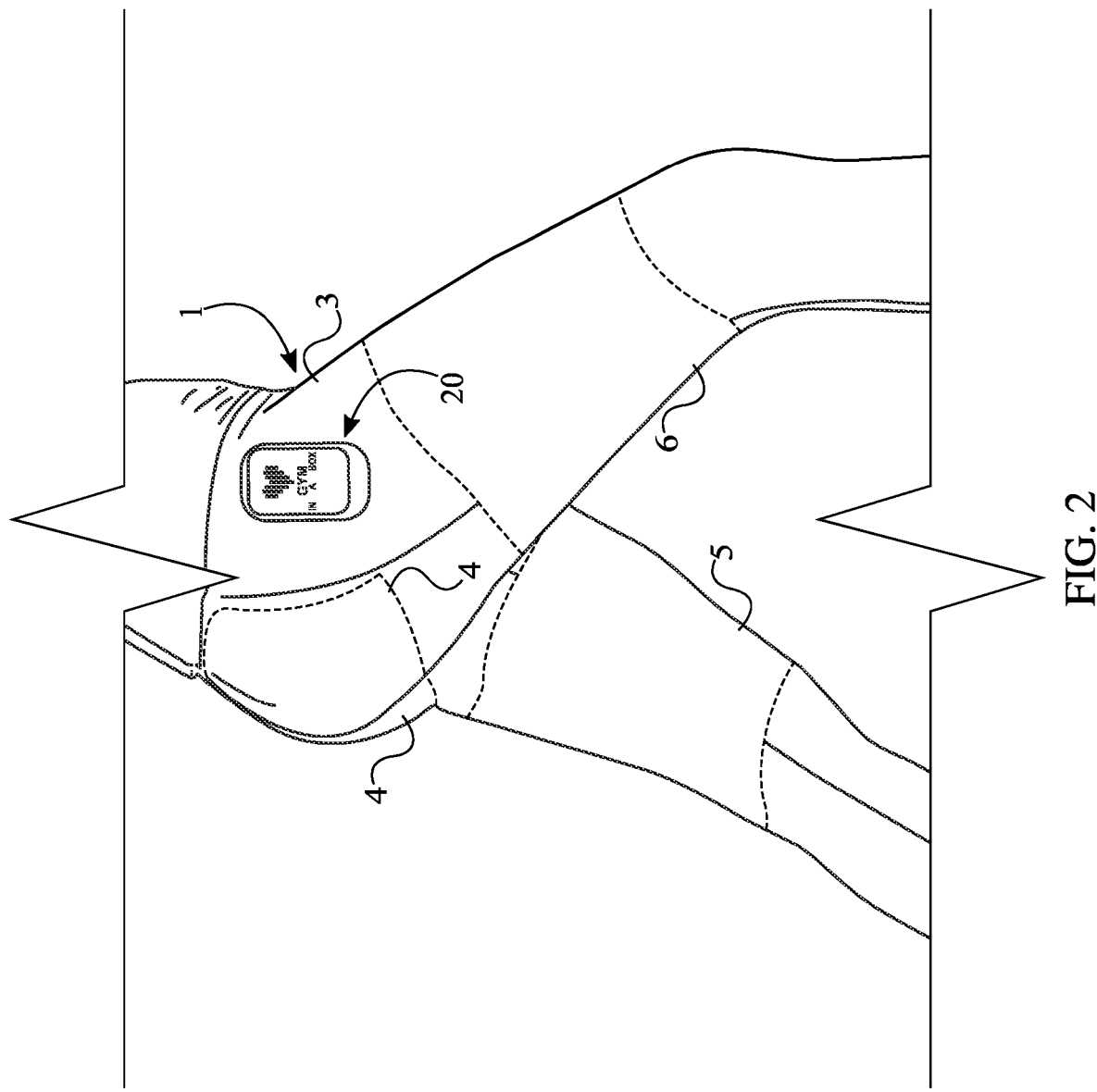
FIG. 2 is a side view of the first embodiment of the present invention.

In a first embodiment of the present invention, the piece of athletic wear 1 is a pair of athletic pants, seen in FIG. 1 and FIG. 2. The pair of athletic pants stimulates and tones the leg muscles of a user. Moreover, the pair of athletic pants stimulates the hamstrings, quads, and glutes of the user. In order to effectively shape and tone the legs of the user, the pair of athletic pants comprises a buttocks-bracing portion 4, at least one left-thigh-bracing portion 5, and at least one right-thigh-bracing portion 6. Each muscle group of both legs are equally targeted as the plurality of muscle-stimulation pads 16 is distributed amongst the buttocks-bracing portion 4, the at least one left-thigh-bracing portion 5, and the at least one right-thigh-bracing portion 6.

In a second embodiment of the present invention, the piece of athletic wear 1 is a waistband, seen in FIG. 3, FIG. 4, FIG. 5, FIG. 6, FIG. 7, FIG. 8, FIG. 9, and FIG. 10. The waistband stimulates and tones the core of the user. More specifically, the abdominal region and the lower back of the user. The waistband comprises a first end 7, a second end 8, an abs-bracing portion 9, and a lower-back-bracing portion 10. The first end 7 and the second end 8 allow the waistband to be adjustable around the waist for any user and connect the waistband around the midsection of the user. The abs-bracing portion 9 wraps around the abdominal region, and the lower-back-bracing portion 10 wraps around the lower back. The abs-bracing portion 9 is positioned adjacent to the first end 7 as the first end 7 presses directly onto the abdominal region of the user. The lower-back-bracing portion 10 is positioned in between the abs-bracing portion 9 and the second end 8 as the area between the abs-bracing portion 9 and the second end 8 directly presses against the lower back of the user. The entire core of the user is simultaneously targeted as the plurality of muscle-stimulation pads 16 is distributed amongst the abs-bracing portion 9 and the lower-back-bracing portion 10.

Figure 3:
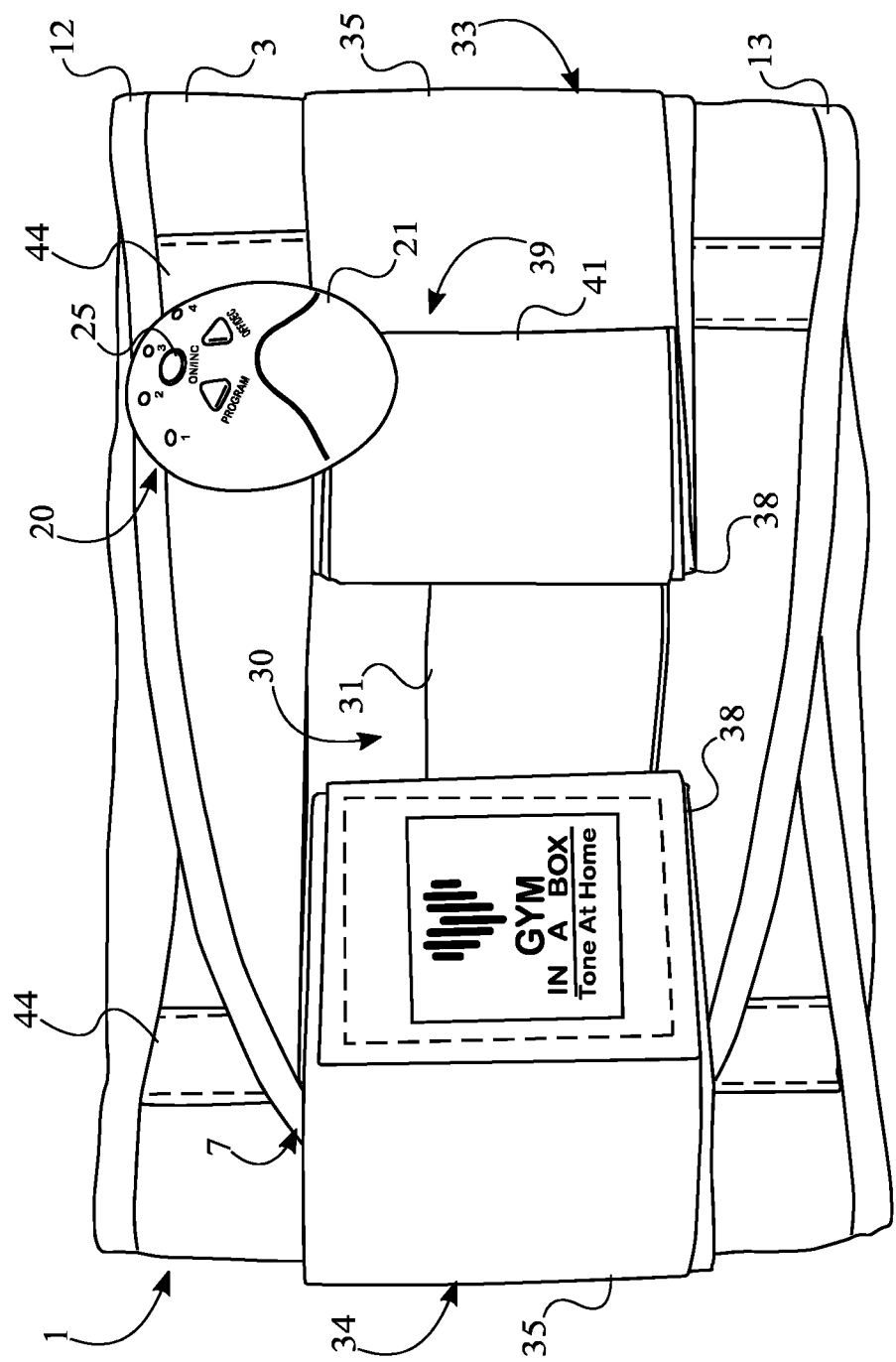
FIG. 3 is a front side view of a second embodiment of the present invention with a first end for a waistband folded on top of a second end of the waistband.
Figure 4:
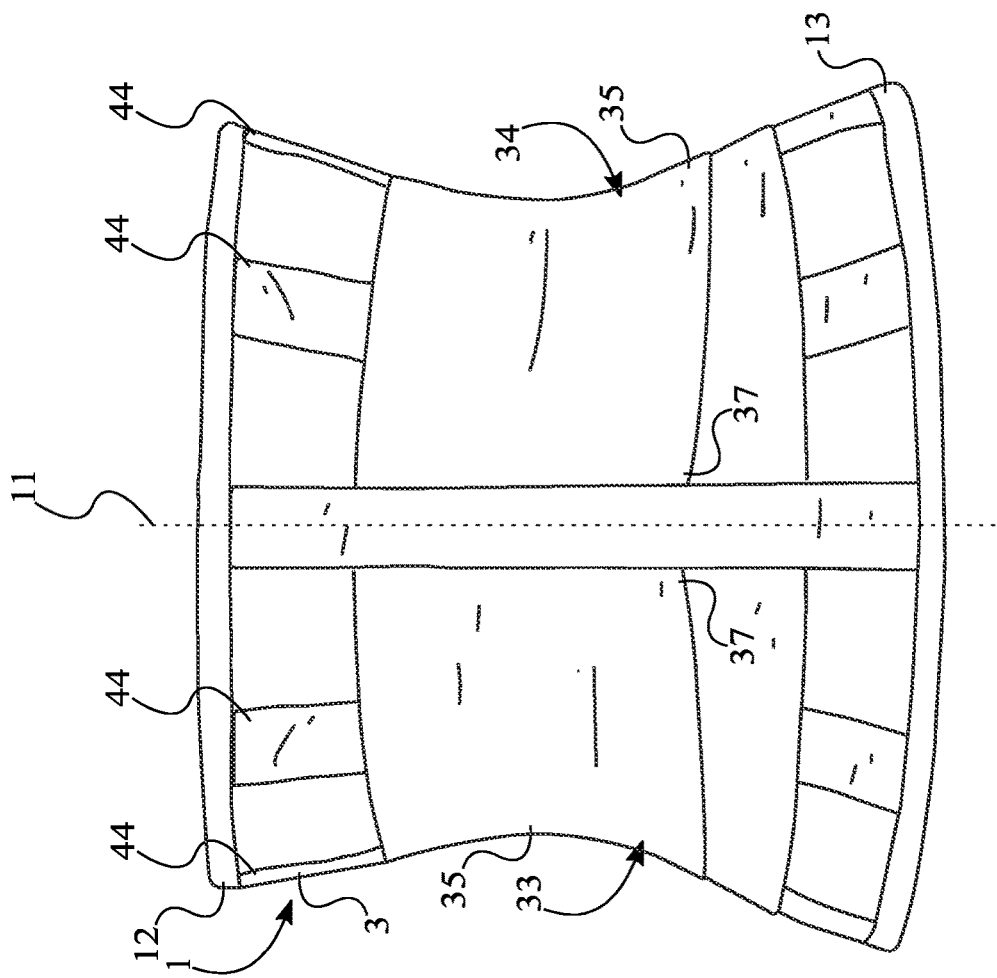
FIG. 4 is a rear side view of the second embodiment of the present invention with a first compression band and a second compression band wrapped tightly around the waistband.
Figure 5:
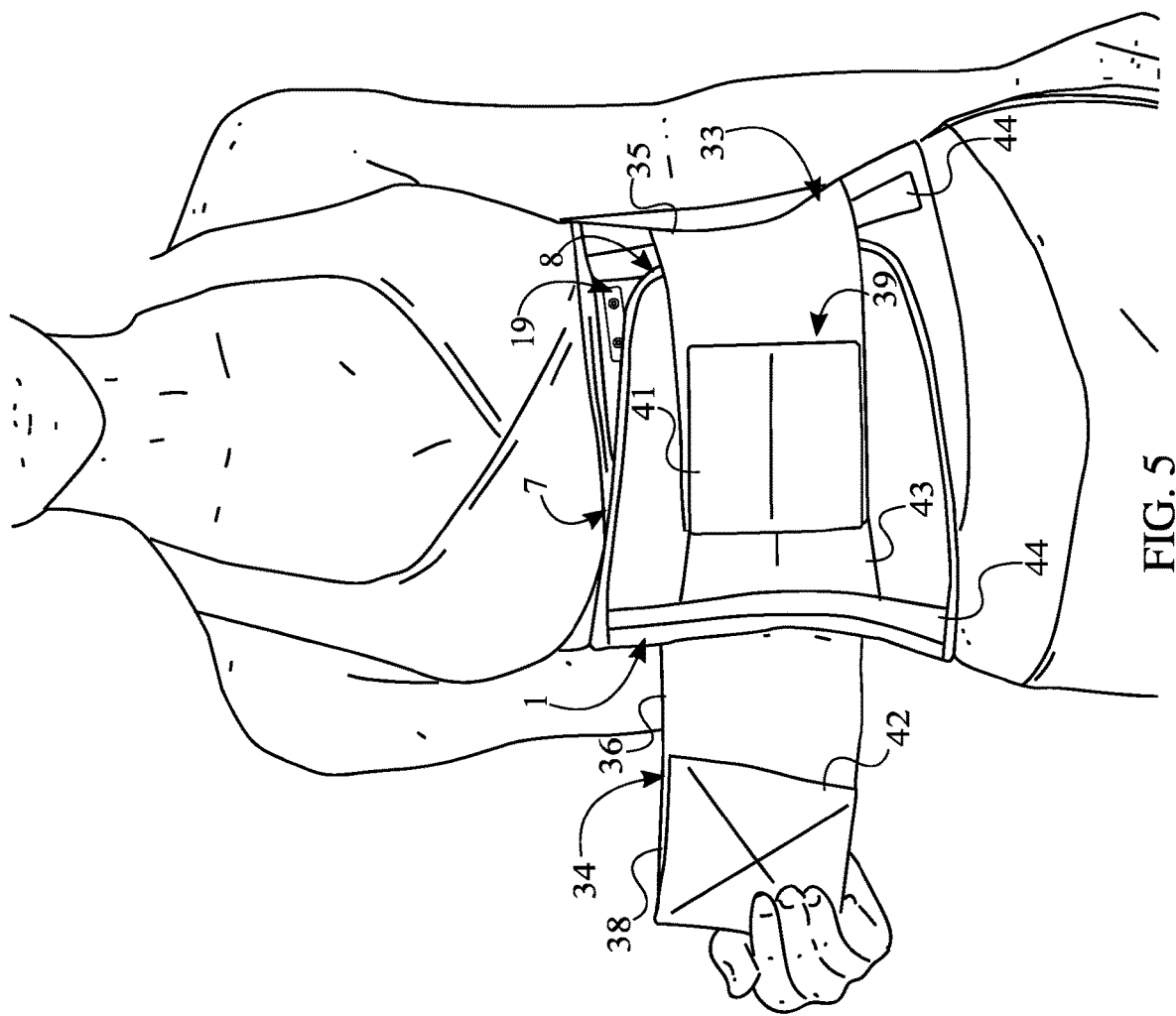
FIG. 5 is a front side view of the second embodiment of the present invention with the second end attached onto the first end of the waistband, the first compression band attached onto the second end of the waistband, and the second compression band detached from the first compression band.
Figure 6:
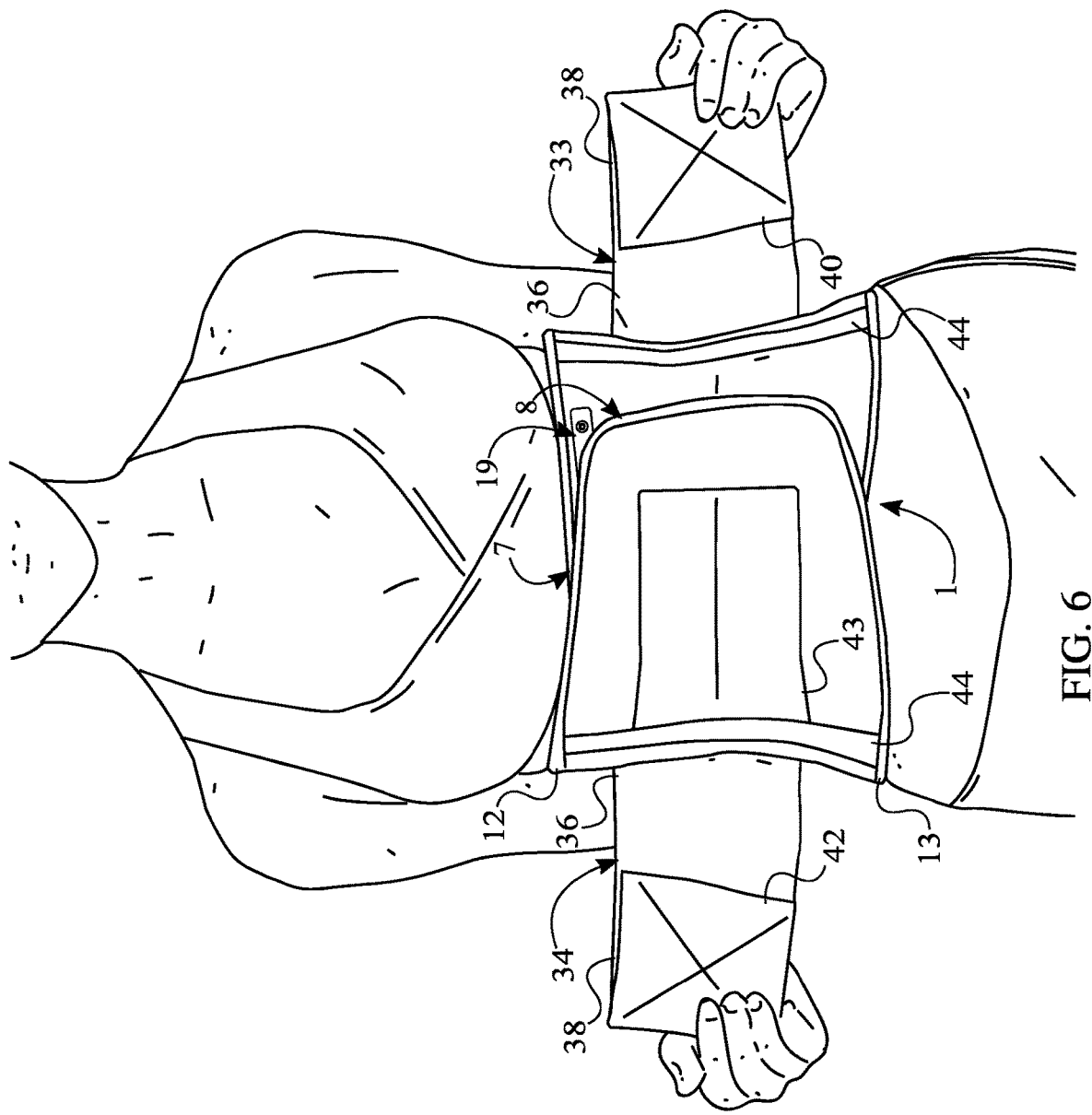
FIG. 6 is a front side view of the second embodiment of the present invention with the second end attached onto the first end of the waistband, the first compression band detached from the waistband, and the second compression band detached from the first compression band.

In order to secure the first end 7 with the second end 8, the second embodiment of the present invention further comprises a first hook-and-loop fastener 30, seen in FIG. 3, FIG. 7, and FIG. 8. In order for the waistband to be length-adjustable around the waist of the user, the first hook-and-loop fastener 30 comprises a first elongated piece 31 and a second elongated piece 32. Moreover, the first elongated piece 31 and the second elongated piece 32 are preferably patches of Velcro. The waistband wraps around the waist of the user as the first elongated piece 31 is positioned adjacent with the first end 7, and the second elongated piece 32 is positioned adjacent with the second end 8. As the second end 8 overlaps with the first end 7, the first elongated piece 31 is fixed onto the outer surface 3, and the second elongated piece 32 is fixed onto the inner surface 2. More specifically, the first elongated piece 31 is releasably engaged with the second elongated piece 32, allowing the user to easily secure, remove, and adjust the waistband around the waist of the user.

The present invention serves as a body shaper as well as the present invention further comprises a first compression band 33 a second compression band 34. The first compression band 33 and the second compression band 34 promote the hourglass physique, seen in FIG. 3, FIG. 4, FIG. 5, and FIG. 6. In order to further tighten the present invention around the waistline of the user, the first compression band 33 and the second compression band 34 each comprises an outer face, an inner face, a fixed end, and a free end. The outer face is oriented away from the waistband, and the inner face is oriented towards the waistband of the user. The fixed end mounts the first compression band 33 and the second compression band 34, respectively, with the waistband. The free end of the second compression band 34 latches onto the free end of the first compression band 33 and allows the first compression band 33 to be length-adjustable with the second compression band 34 around the waist of any user. The first compression band 33 and the second compression band 34 are tightened around the waist of the user as the inner surface 2 of the first compression band 33 and the inner surface 2 of the second compression band 34 are positioned adjacent with the outer face. Moreover, the first compression band 33 and the second compression band 34 are positioned adjacent with each other. Both the first compression band 33 and the second compression band 34 are centrally aligned with the waistband as the fixed end is fixed adjacent with a central widthwise axis 11 of the waistband. The central widthwise axis 11 is equidistant between the first end 7 of the waistband and the second end 8. In order to secure the position of the first compression band 33, and consequently the second compression band 34, with the waistband, the free end of the first compression band 33 is releasably attached with the second end 8. The user is able to tighten or loosen the second compression band 34 with the first compression band 33 as the free end of the second compression band 34 is releasably attached with the free end of the first compression band 33.

Similar with the waistband, the present invention further comprises second hook-and-loop fastener 39 in order to securely fasten the second compression band 34 with the first compression band 33 and the first compression band 33 with the waistband, seen in FIG. 3, FIG. 5, FIG. 6, and FIG. 10. The second hook-and-loop fastener 39 comprises a first patch piece 40, a second patch piece 41, a third patch piece 42, and a third elongated piece 43. The first patch piece 40 and the third elongated piece 43 latches the first compression band 33 onto the waistband. The second patch piece 41 and the third patch piece 42 latches the second compression band 34 onto the first compression band 33. The third elongated piece 43 is fixed adjacent with the second end 8. In order to efficiently connect the first compression band 33 with both the waistband and the second compression band 34, the first patch piece 40 and the second patch piece 41 are positioned adjacent with the free end of the first compression band 33. The first compression band 33 connects with the waistband as the third patch piece 42 is positioned adjacent with the free end of the second compression band 34. More specifically, the first patch piece 40 is fixed onto the inner surface 2 of the first compression band 33, and the second patch piece 41 is fixed onto the outer surface 3 of the first compression band 33. Furthermore, the third patch piece 42 is fixed onto the inner surface 2 of the second compression band 34 as the inner surface 2 of the second compression band 34 presses against the outer surface 3 of the first compression band 33. The position of the first compression band 33, and consequently the second compression band 34, is secured with the waistband as the first patch piece 40 is releasably engaged with the third elongated piece 43. The second compression band 34 is adjustable with the first compression band 33 as the third patch piece 42 is releasably engaged with the second patch piece.

The second embodiment of the present invention further comprises a plurality of flexible reinforcement members 44, seen in FIG. 3, FIG. 4, FIG. 5, FIG. 6, FIG. 7, FIG. 8, FIG. 9, and FIG. 10 In order to fully extend the waistband about the abdominal region of the user, the present invention further comprises a plurality of flexible reinforcement members 44. The plurality of flexible reinforcement members 44 prevents the waistband from crumpling in on itself while the user moves and performs a variety of exercises. The structural integrity of the waistband is evenly reinforced as the plurality of flexible reinforcement members 44 is distributed along the waistband. The waistband further comprises a first lengthwise edge 12 and a second lengthwise edge 13. More specifically, the first lengthwise edge 12 is positioned adjacent the chest of the user, and the second lengthwise edge 13 adjacent the hips of the user. The first lengthwise edge 12 is positioned opposite the second lengthwise edge 13 across the waistband. The structural integrity of the waistband is evenly reinforced as the plurality of flexible reinforcement members 44 is distributed along the waistband. The waistband extends over the entirety of the abdominal region as each of the plurality of flexible reinforcement members 44 is perpendicularly positioned in between the first lengthwise edge 12 and the second lengthwise edge 13. The plurality of flexible reinforcement members 44 is integrated into the waistband, thereby maintaining a smooth inner surface 2 and a smooth outer surface 3 for the waistband.

Figure 11:
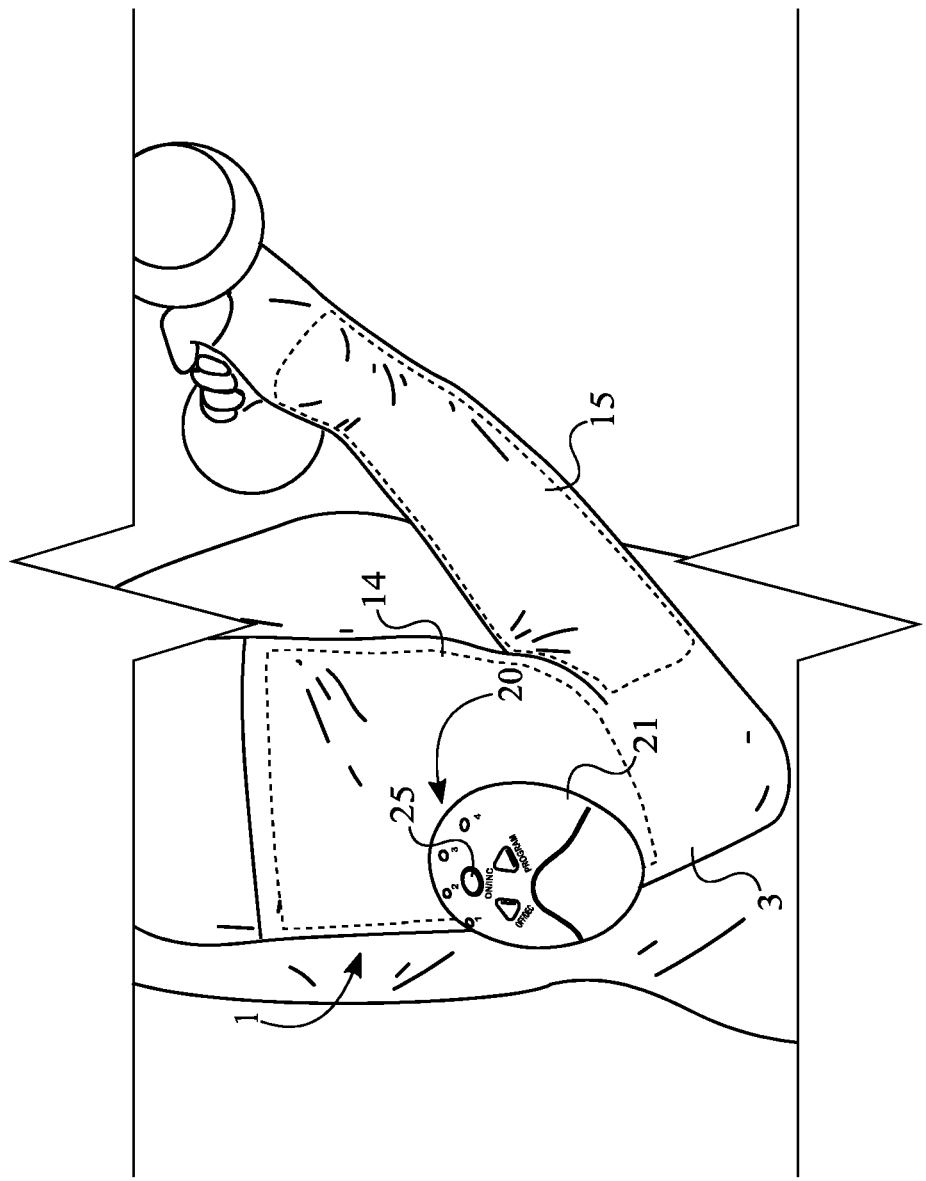
FIG. 11 is a front side view of a third embodiment of the present invention.
Figure 12:
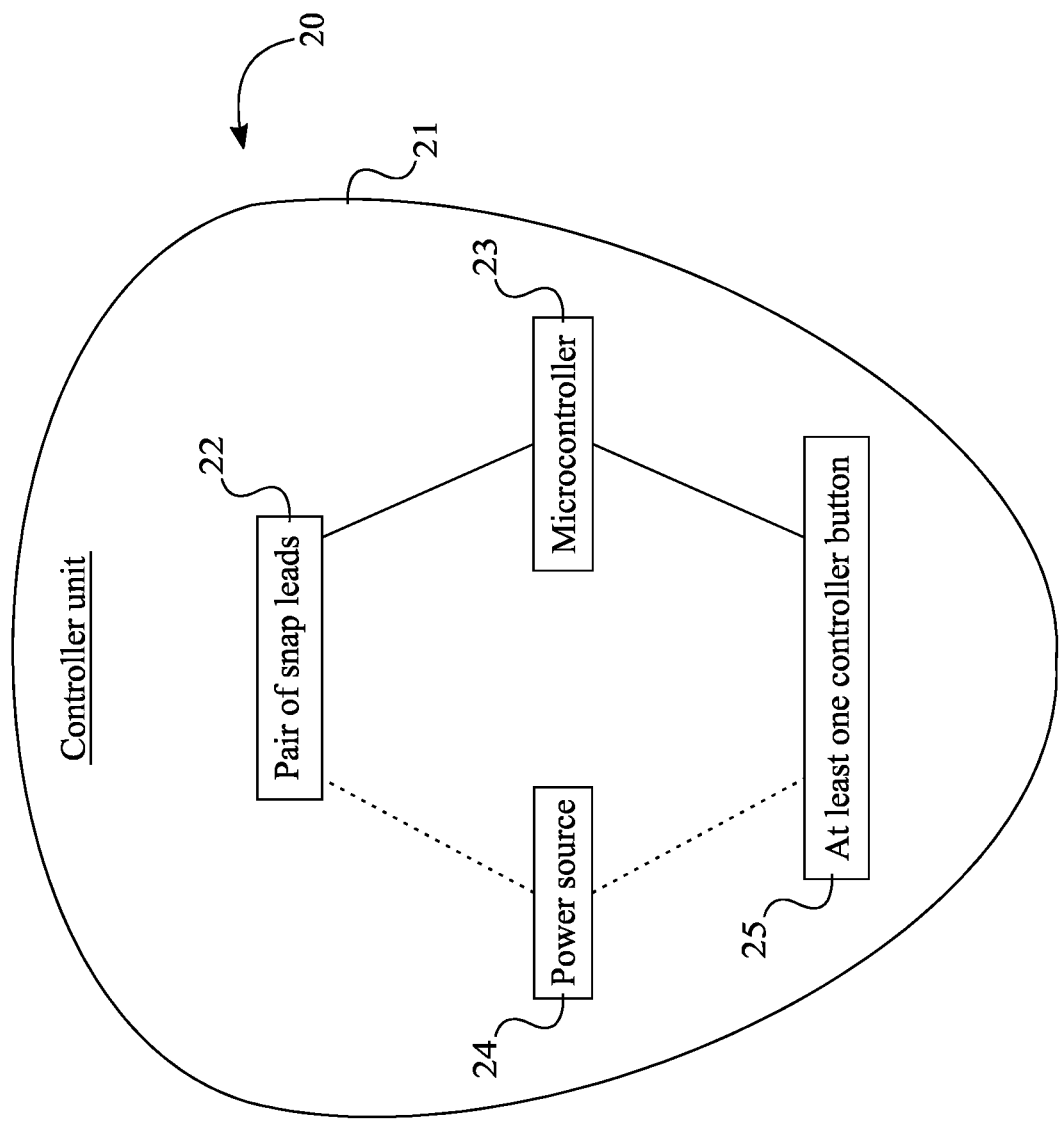
FIG. 12 is a schematic view of the electronic connections for a controller unit of the present invention.

In a third embodiment of the present invention, the piece of athletic wear 1 is an arm sleeve, seen in FIG. 11. The arm sleeve stimulates and tones the arm muscles of a user. Moreover, the arm sleeve stimulates the biceps, triceps, and forearm of the user. In order to effectively shape and tone the arms of the user, the arm sleeve comprises an arm-bracing portion 14 and a forearm-bracing portion 15. The arm sleeve contours around the arm of the user as the arm-bracing portion 14 is positioned adjacent with the forearm-bracing portion 15. Each muscle group of the arm is equally targeted as the plurality of muscle-stimulation pads 16 is distributed amongst the arm-bracing portion 14.

Although the invention has been explained in relation to its preferred embodiments, it is to be understood that many other possible modifications and variations can be made without departing from the spirit and scope of the invention as hereinafter claimed.

What is claimed is:

1. A muscle-stimulating athletic wear comprising:
a piece of athletic wear;
a plurality of muscle-stimulation pads;
a pair of conductive snaps;
a controller unit;
the piece of athletic wear comprising an inner surface and an outer surface;
the controller unit comprising a housing, a pair of snap leads, a microcontroller, and a power source;
the plurality of muscle-stimulation pads being fixed onto the inner surface;
the pair of conductive snaps being integrated through the piece of athletic wear;
the plurality of muscle-stimulation pads being electrically connected to the pair of conductive snaps;
the pair of snap leads being externally mounted with the housing;
the power source and the microcontroller being mounted within the housing;
the pair of snap leads being electronically connected with the microcontroller;
the pair of snap leads being electrically connected with the power source; and,
each of the pair of snap connectors being releasably engaged by a corresponding lead from the pair of snap leads;
wherein the muscle-stimulating athletic wear further comprises at least one flat conductor,
the plurality of muscle-stimulation pads comprises a plurality of first pads and a plurality of second pads;
the plurality of first pads being positioned adjacent to the pair of conductive snaps;
the plurality of second pads being positioned adjacent to the pair of conductive snaps;
the plurality of flat conductors being mounted onto the inner surface;
each of the plurality of first pads being in direct electrical communication with the pair of conductivity snaps; and,
each of the plurality of second pads being in indirect electrical communication with the pair of conductivity snaps by the at least one flat conductor.

2. The muscle-stimulating athletic wear as claimed in claim 1, wherein each of plurality of muscle-stimulation pad is a piece of silver-embedded stretch fabric, and wherein the piece of silver-embedded stretch fabric is electrically conductive.

3. The muscle-stimulating athletic wear as claimed in claim 1 comprising:
the at least one flat conductor comprising an insulative tape and a strip of silver-embedded stretch fabric;
the strip of silver-embedded stretch fabric being electrically conductive; and,
the strip of silver-embedded stretch fabric being thermally adhered onto the inner surface by the insulative tape.

4. The muscle-stimulating athletic wear as claimed in claim 1 comprising:
a pair of electrically-insulative covers;
the pair of electrically-insulative covers being positioned adjacent to the inner surface; and,
each of the pair of electrically-insulative covers being mounted onto a corresponding snap from the pair of conductive snaps.

5. The muscle-stimulating athletic wear as claimed in claim 1 comprising:
the controller unit further comprising at least one controller button;
the pair of snap leads being positioned offset from each other;
the at least one controller button being externally mounted with the housing;
the at least one controller button being electronically connected with the microcontroller; and,
the at least one controller button being electrically connected with the power source.

6. The muscle-stimulating athletic wear as claimed in claim 1 comprising:
the piece of athletic wear being a pair of athletic pants;
the pair of athletic pants comprising a buttocks-bracing portion, at least one left-thigh-bracing portion, and at least one right-thigh-bracing portion; and,
the plurality of muscle-stimulation pads being distributed amongst the buttocks-bracing portion, the at least one left-thigh-bracing portion, and the at least one right-thigh-bracing portion.

7. The muscle-stimulating athletic wear as claimed in claim 1 comprising:
the piece of athletic wear being a waistband;
the waistband comprising a first end, a second end, an abs-bracing portion, and a lower-back-bracing portion;
the abs-bracing portion being positioned adjacent to the first end;
the lower-back-bracing portion being positioned in between the abs-bracing portion and the second end; and,
the plurality of muscle-stimulation pads being distributed amongst the abs-bracing portion and the lower-back-bracing portion.

8. The muscle-stimulating athletic wear as claimed in claim 7 comprising:
a first hook-and-loop fastener;
the first hook-and-loop fastener comprising a first elongated piece and a second elongated piece;
the first elongated piece being positioned adjacent with the first end;
the second elongated piece being positioned adjacent with the second end;
the first elongated piece being fixed onto the outer surface;
the second elongated piece being fixed onto the inner surface; and,
the first elongated piece being releasably engaged with the second elongated piece.

9. The muscle-stimulating athletic wear as claimed in claim 7 comprising:
a first compression band;
a second compression band;
the first compression band and the second compression band each comprising an outer face, an inner face, a fixed end, and a free end;
the inner face of the first compression band and the inner face of the second compression band being positioned adjacent with the outer surface;
the first compression band and the second compression band being positioned adjacent with each other;

the fixed end being fixed adjacent with a central widthwise axis of the waistband;
the free end of the first compression band being releasably attached with the second end; and,
the free end of the second compression band being releasably attached with the free end of the first compression band.

10. The muscle-stimulating athletic wear as claimed in claim 9 comprising:
a second hook-and-loop fastener;
the second hook-and-loop fastener comprising a first patch piece, a second patch piece, a third patch piece, and a third elongated piece;
the third elongated piece being fixed adjacent the second end;
the first patch piece and the second patch piece being positioned adjacent with the free end of the first compression band;
the third patch piece being positioned adjacent with the free end of the second compression band;
the first patch piece being fixed onto the inner surface of the first compression band;
the second patch piece being fixed onto the outer surface of the first compression band;
the third patch piece being fixed onto the inner surface of the second compression band;
the first patch piece being releasably engaged with the third elongated piece; and,
the third patch piece being releasably engaged with the second patch piece.

11. The muscle-stimulating athletic wear as claimed in claim 7 comprising:
a plurality of flexible reinforcement members;
the waistband further comprising a first lengthwise edge and a second lengthwise edge;
the first lengthwise edge being positioned opposite the second lengthwise edge across the waistband;
the plurality of flexible reinforcement members being distributed along the waistband;
each of the plurality of flexible reinforcement members being perpendicularly positioned in between the first lengthwise edge and the second lengthwise edge; and,
the plurality of flexible reinforcement members being integrated into the waistband.

12. The muscle-stimulating athletic wear as claimed in claim 1 comprising:
the piece of athletic wear being an arm sleeve;
the arm sleeve comprising an arm-bracing portion and a forearm-bracing portion;
the arm-bracing portion being positioned adjacent with the forearm bracing portion; and,
the plurality of muscle-stimulation pads being distributed amongst the arm-bracing portion.

* * * * *